United States Patent
Park (10) Patent No.: US 7,756,575 B2
(45) Date of Patent: Jul. 13, 2010

(54) APPARATUS AND METHOD OF DIAGNOSING HEALTH USING CUMULATIVE DATA PATTERN ANALYSIS VIA FAST FOURIER TRANSFORMATION OF BRAIN WAVE DATA MEASURED FROM FRONTAL LOBE

(75) Inventor: Pyong-Woon Park, Daejeon (KR)

(73) Assignee: Braintech Corporation, Seoul (KR)

(*) Notice: Subject to any disclaimer, the term of this patent is extended or adjusted under 35 U.S.C. 154(b) by 113 days.

(21) Appl. No.: 12/066,326

(22) PCT Filed: Sep. 5, 2006

(86) PCT No.: PCT/KR2006/003526

§ 371 (c)(1),
(2), (4) Date: Mar. 10, 2008

(87) PCT Pub. No.: WO2007/032617

PCT Pub. Date: Mar. 22, 2007

(65) Prior Publication Data

US 2008/0200826 A1    Aug. 21, 2008

(30) Foreign Application Priority Data

Sep. 14, 2005   (KR) .................. 10-2005-0085637

(51) Int. Cl.
*A61B 5/04* (2006.01)
(52) U.S. Cl. ..................... 600/544; 600/545
(58) Field of Classification Search ............. 600/544, 600/545

See application file for complete search history.

(56) References Cited

U.S. PATENT DOCUMENTS

| | | | |
|---|---|---|---|
| 3,971,366 A | | 7/1976 | Motoyama |
| 4,794,533 A | * | 12/1988 | Cohen ................ 600/544 |
| 6,097,980 A | | 8/2000 | Monastra et al. |
| 6,126,595 A | | 10/2000 | Amano et al. |
| 6,272,378 B1 | | 8/2001 | Baumgart-Schmitt |
| 6,317,627 B1 | | 11/2001 | Ennen et al. |

(Continued)

FOREIGN PATENT DOCUMENTS

KR    1020010103920 A    11/2001

(Continued)

*Primary Examiner*—Robert L Nasser
*Assistant Examiner*—Michael D'Angelo
(74) *Attorney, Agent, or Firm*—Larson & Anderson, LLC (57) ABSTRACT

Provided is a health diagnosis apparatus and method in which brain waves are sequentially measured from the frontal lobe of a human body that is to be diagnosed when the eyes are in an eyes-open and eyes-closed state, the measured brain waves are fast Fourier transformed to then be accumulated, and then the health conditions of the respective portions of the human body can be determined according to the patterns with respective frequencies. The health condition diagnosis method includes measuring brain waves; performing a fast-Fourier-transform on the measured brain waves; classifying the frequency-based brain wave data into opened and closed eye state brain waves to thus accumulate the classified result; finding a specific frequency and a pattern thereof which repeats from the accumulated brain wave data; correspondingly connecting the frequency and the respective portions of the human body based on the specific frequency pattern; and determining the health condition of the human body. The frequency-based health condition determination is based on clinic test results.

10 Claims, 3 Drawing Sheets

U.S. PATENT DOCUMENTS

| | | | |
|---|---|---|---|
| 6,358,201 B1 | 3/2002 | Childre et al. | |
| 7,177,676 B2 * | 2/2007 | Setiabudi et al. | 600/545 |
| 2003/0139683 A1 | 7/2003 | Ryu et al. | |
| 2006/0111644 A1 * | 5/2006 | Guttag et al. | 600/544 |

FOREIGN PATENT DOCUMENTS

| | | |
|---|---|---|
| KR | 1020040021269 A | 3/2004 |

* cited by examiner

APPARATUS AND METHOD OF DIAGNOSING HEALTH USING CUMULATIVE DATA PATTERN ANALYSIS VIA FAST FOURIER TRANSFORMATION OF BRAIN WAVE DATA MEASURED FROM FRONTAL LOBE

TECHNICAL FIELD

The present invention relates to an apparatus and method for diagnosing the health of an individual through brain wave pattern analysis, and more particularly, to a health diagnosis apparatus and method in which brain waves are sequentially measured from the frontal lobe of a human body that is diagnosed when the eyes of an individual are opened and closed, the measured brain waves are fast Fourier transformed to then be accumulated, and then the health condition of respective portions of the human body can be determined according to patterns with respective frequencies obtained by fast Fourier transforming the brain waves.

BACKGROUND ART

Brain waves are electrical signals of the brain measured on the scalp of a human, and the physical values of the brain waves reflect the state of the human with an electrical potential difference of several tens of micro-volts and a frequency of 30 Hz or less. There are four kinds of brain waves called the alpha wave, the beta wave, the theta wave and the delta wave. The beta wave is the brain wave at a frequency of 13 Hz or greater and is generated when the mental activity of a human is active. The alpha wave is the brain wave in a frequency range of 8-13 Hz and is generated when the brain of a human is in rest or in a stabilized state, which represents a typical brain wave of an adult. The theta wave is a brain wave in a frequency range of 4-7 Hz and is generated during a general dormant state. The delta wave is the typical brain wave in a frequency range of 0.5-3 Hz and is generated during a deep and sound sleep state. Up to the present, extensive research has been conducted on the study of brain waves. However, the research has not succeeded in sufficiently analyzing the information contained in brain waves. And as such, the interpretation of brain waves still remains unanalyzed.

There are a method of interpreting brain waves in the time domain and a method of interpreting brain waves in the frequency domain. However, the method of interpreting brain waves in the time domain requires much experience and skill, and it is difficult to discriminate the minute differences between brain waves by using such method. Presently, a frequency analysis method, which has been widely used in interpreting brain waves, needs to process the measured signals in order to easily analyze the state of the human body to be diagnosed in real-time.

A conventional brain wave measuring apparatus mainly uses cup-shaped electrodes, which are adhered to the scalp of the human head using a paste. Furthermore, a separately built-in card has to be included in a computer for analyzing the brain waves in order to receive and analyze a plurality of channels of the measured brain waves.

Korean Patent Laid-open Publication No. 99-46503 entitled "Real-time brain wave measuring apparatus using headband" on Jul. 5, 1999, which was registered as Korean Patent Registration No. 282733 on Nov. 30, 2000 entails this matter. However, the real-time brain wave measuring apparatus does not employ any pastes but is still able to measure brain waves from the scalp of the human head.

Moreover, brain waves are not only used for determining the health condition of the brain itself, but in addition, it is also important to distinguish brain waves from other signals (referred to as miscellaneous waves) that are generated from other portions of the human body other than the brain, and to remove the miscellaneous waves from the brain waves so as to extract only the pure brain waves. Thus, the above-mentioned conventional art has failed to determine the health condition of an individual using the miscellaneous waves.

As such, in order to use the miscellaneous waves that are generated from respective portions of the human body, the miscellaneous waves need to be minimally removed from the brain waves and correspond to the brain waves due to the fact that the respective frequencies of the miscellaneous waves and of the brain waves are in a one-to-one correspondence relationship so as to determine the health condition of an individual. However, the conventional art has failed to determine the health condition of an individual using the one-to-one correspondence relationship between the frequencies of the miscellaneous waves and of the brain waves.

DETAILED DESCRIPTION OF THE INVENTION

Technical Problem

The present invention provides an apparatus and method for diagnosing health through brain wave pattern analysis, in which miscellaneous waves are minimally removed from the brain waves which are measured from the scalp of a human body that is to be diagnosed, and then the brain waves are accumulated for a predetermined time to then determine the health condition of respective portions of the human body according to a one-to-one correspondence relationship between the patterns of the respective frequencies of the brain waves and the miscellaneous waves generated from the respective portions of the human.

Technical Solution

According to an aspect of the present invention, there is provided a health diagnosis apparatus using brain wave pattern analysis from brain wave signals measured in a brain wave measuring unit that measures brain waves via brain wave measuring sensors attached to the frontal lobe of a human body that is to be diagnosed, the health diagnosis apparatus comprising a brain wave analysis computer that receives and fast-Fourier-transforms the measured brain waves, accumulates brain wave data for a predetermined time, analyzes a pattern of a signal with respective frequencies, and sets the analyzed frequency pattern to correspond to the respective portions of the human body, to thereby determine a health condition of the human body.

The brain wave analysis computer may accumulate the measured brain wave data for the predetermined time, to thereby find a point of inflection to discover a curve changing point hourly according to the respective frequencies and to extract a repetitively occurring inflection frequency, and then determines the health condition of the human body from the extracted inflection frequency using a database storing frequency data of the respective portions of the human body in a one-to-one correspondence relationship with the respective frequencies which are discovered from clinical test results.

According to another aspect of the present invention, there is also provided a method of diagnosis health through brain wave pattern analysis, the health condition diagnosis method comprising adhering a two-channels brain wave measuring sensor to the frontal lobe of the human body to thus measure brain waves in which an ear clip is a base electrode and the forehead center is a reference electrode; fast-Fourier-transforming the measured brain waves; accumulating the fast-Fourier-transformed data for a predetermined time; analyzing a pattern of a signal with respective frequencies; and setting the analyzed frequency pattern to be in a one-to-one correspondence relationship with the respective portions of the human body, to thereby determine the health condition of the human body.

The pattern analysis step may comprise discovering an inflection point hourly according to the respective frequencies, and extracting a repetitively occurring inflection frequency.

The health condition determination may be performed using a health condition determination equation of human bodies in which a relative severity of a disease at the corresponding portion of the human body corresponding to a certain frequency is proportional to the number of inflections and amplitude of the brain wave signal and is inversely proportional to a full width at a half maximum (FWHM) value of the brain wave signal, according to the number of inflections, amplitude of the brain wave signal and the FWHM value of the brain wave signal.

Advantageous Effects

As described above, an apparatus and method for diagnosing health according to the present invention simply and easily diagnoses the health condition as well as the brain condition of an individual through brain waves measured from the frontal lobe of the human body.

Best Mode

Herein below, an apparatus and method for diagnosing health through brain wave pattern analysis according to embodiments of the present invention will be described with reference to the accompanying drawings. Like reference numerals and symbols denote like elements through the following embodiments.

In the case of an apparatus and method for diagnosing health through brain wave pattern analysis according to an embodiment of the present invention, a two-channels brain wave measuring unit is adhered to the frontal lobe of a human head to thus measure brain waves and an ear-clip is a base electrode and the forehead center is a reference electrode. The measured brain waves are fast Fourier transformed. Then, the fast-Fourier-transformed data is accumulated for a predetermined time and a pattern of a signal with respective frequencies is analyzed. The analyzed frequency pattern is set to be in a one-to-one correspondence relationship with the respective portions of the human body. As a result, the health condition of the human body can be determined.

In the present invention, the brain wave data that is measured by the two-channels brain wave measuring unit, which is adhered to the frontal lobe located in the forehead of the human body, is transmitted to a computer using a serial communication method or a universal serial bus (USB) communication method, and then fast-Fourier-transformed. During the measurement of the brain waves, the human body is diagnosed by repeatedly alternating between an eyes-open state and eyes-closed state, so that brain wave data can be collected to observe the appearance and disappearance of basic rhythmic movement and disappearance states of respective bands. The measured brain wave data is accumulated for a predetermined time to thus discover an inflection point according to frequency on an hourly basis, and thus extract a repetitively occurring inflection frequency. The health condition of the human body is determined from the extracted inflection frequency according to a database of respective portions of the human body having a one-to-one correspondence relationship with the respective frequencies discovered from clinical test results. The extracted inflection frequency represents a frequency at a vertex at the point of which a first differential value according to the frequency is obtained and whose slope sign value changes relative to the first differential value. The first differential value is obtained from the following Equations 1 and 2.

$$\text{Delta } 1 = V(f2) - V(f1) \qquad \text{[Equation 1]}$$

$$\text{Delta } 2 = V(f3) - V(f2) \qquad \text{[Equation 2]}$$

Here, f1, f2 and f3 mean frequencies, and V means the intensity of voltage for each frequency f1, f2 and f3. If Delta 1 is a positive value and Delta 2 is a negative value, the frequency f2 is a vertex. A reoccurring of a vertex at an identical frequency means that the brain or body of an individual is active. The brain wave signal represents the condition of the brain and the muscle signal represents the condition of the body. Each inflection frequency is made to correspond to the respective portions of the human body to thereby determine the overall health condition of the human body. The severity of the health condition of the human body is determined by the number of inflections, amplitude of the brain wave signal, and a full width at half maximum (FWHM) value of the brain wave signal, in which a vertex occurs at a predetermined frequency. If the vertex continuously occurs at the predetermined frequency in the eyes-open state and eyes-closed state, it can be determined that the symptoms of a disease are serious in terms of the health condition of the human body. The developing stage of a disease is determined by the FWHM value of the brain wave signal. If the FWHM value of the of the brain wave signal low, it means that a disease has locally spread, and if the FWHM value of the brain wave signal is high, it means that the disease has extensively spread. This can be expressed through Equation 3.

$$H(n,V,w) = Af(nV/w) \qquad \text{[Equation 3]}$$

Here, n denotes the number of inflections, V denotes an amplitude of the brain wave signal, w denotes a FWHM value of the brain wave signal, A denotes a proportion constant, H denotes a function representing health condition, and f denotes a function of the variables n, V and w. Thus, the severity of a disease at a corresponding point of the human body corresponding to a predetermined frequency is proportional to the number of inflections, and amplitude of the brain wave signal, and inversely proportional to the FWHM value of the brain wave signal. This results in a linear equation but can also result in a nonlinear equation.

MODE OF THE INVENTION

Hereinafter, an embodiment of the present invention will be described below with reference to the accompanying drawings.

Figure 1:
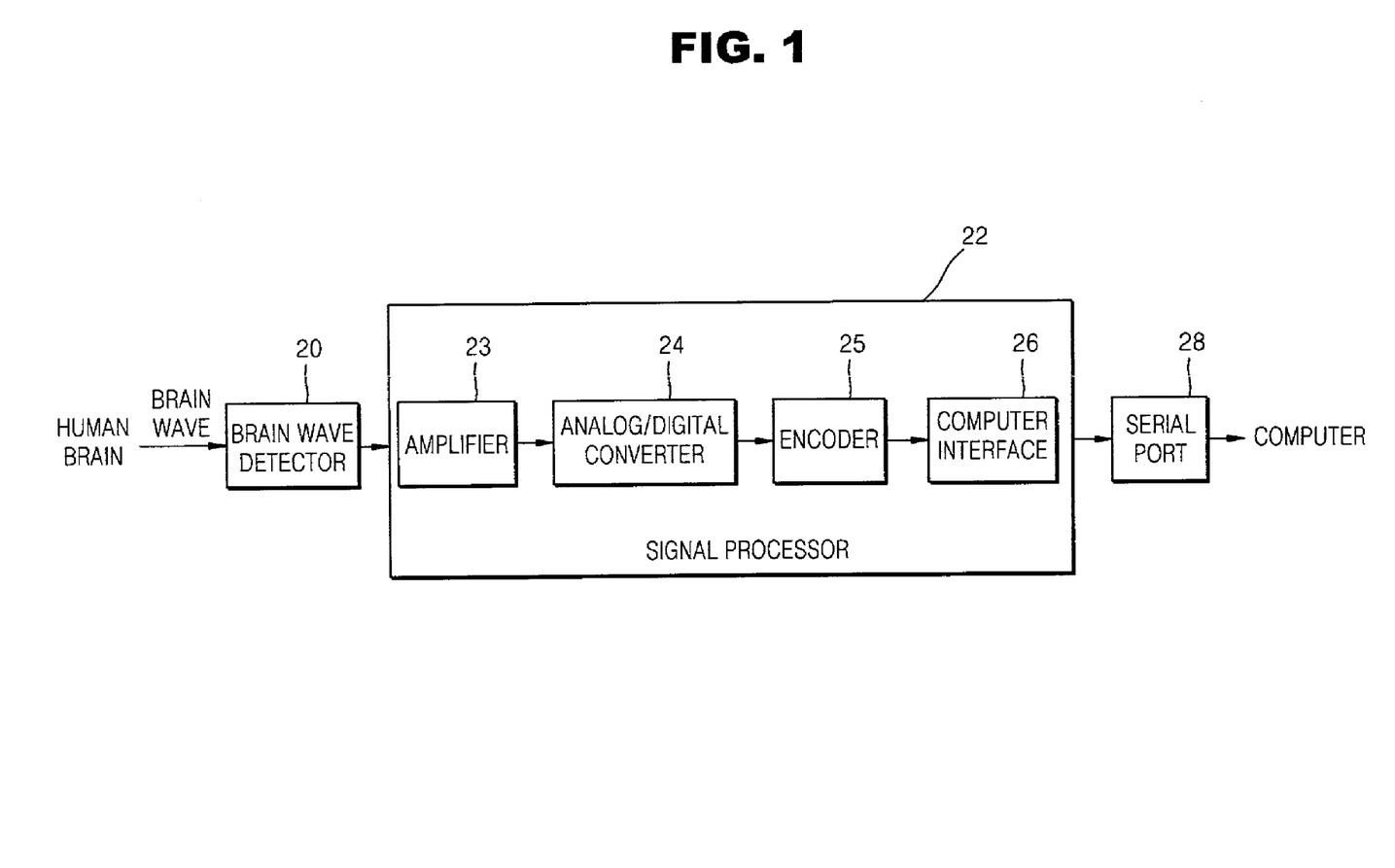
FIG. 1 is a block diagram illustrating a brain wave measuring unit, which measures and processes the brain waves in a health diagnosis apparatus for brain wave pattern analysis, according to an embodiment of the present invention.
Figure 2:
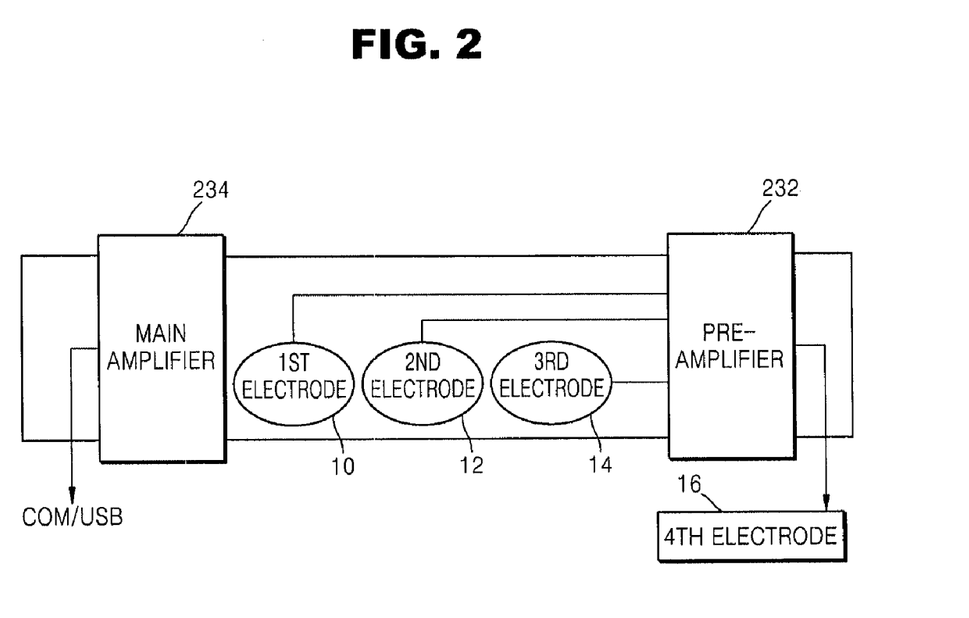
FIG. 2 is a schematic diagram illustrating an amplifier in a headband adhered to the frontal lobe of a human head for measuring and extracting the brain waves, according to an embodiment of the present invention.
Figure 3:
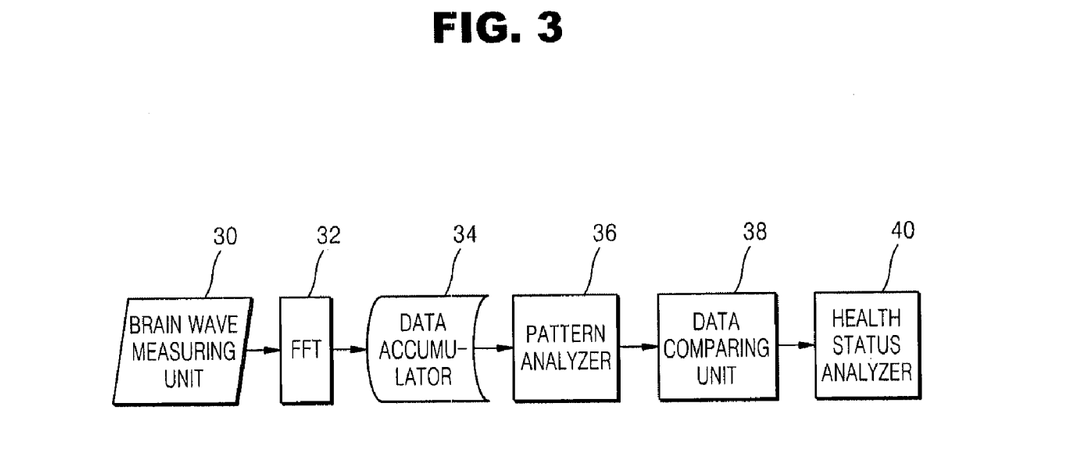
FIG. 3 is a block diagram illustrating a health diagnosis apparatus according to an embodiment of the present invention.
Figure 4:
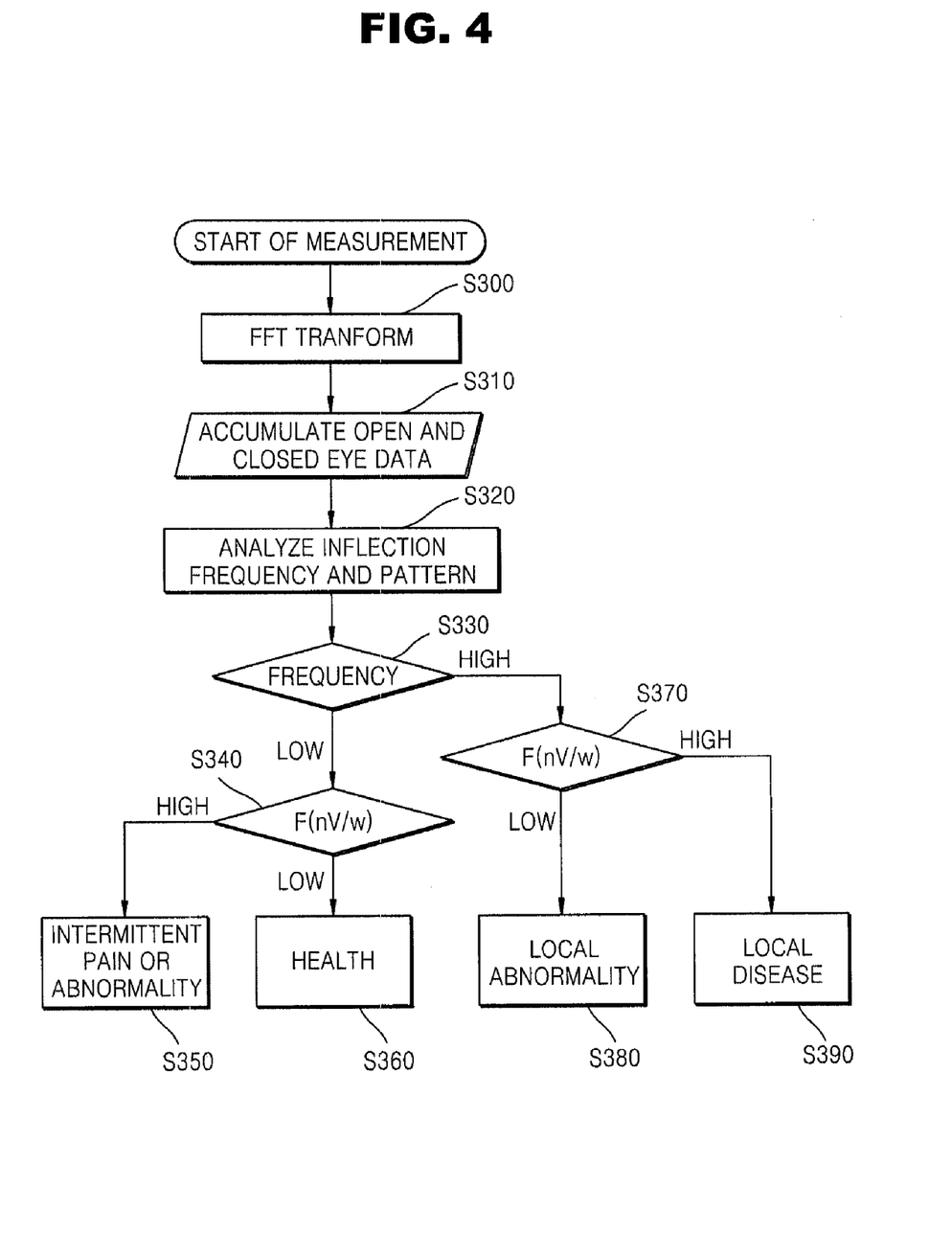
FIG. 4 is a flowchart view illustrating a health diagnosis method, which finds an inflection frequency and analyzes the number of inflections and amplitude of the brain wave signal, and a full width at half maximum (FWHM) value of the brain wave signal, so as to then compare the analyzed result with that of a frequency-based human body correspondence database.

A health diagnosis apparatus for respective frequencies according to the present invention performs a fast-Fourier-transform (FFT) of brain wave data measured from the frontal lobe of the human body that is to be diagnosed, so as to then classify the brain wave data according to the respective frequencies, and accumulates the classified brain wave data for a predetermined time to obtain the occurrence of a repeated particular frequency. The health diagnosis apparatus according to the present invention includes a brain wave measuring unit for measuring brain waves and a health condition diagnosis unit for receiving the measured brain waves and diagnosing the health condition of the human body. The brain wave measuring unit is illustrated in FIGS. 1 and 2, but the health condition diagnosis unit is not illustrated in the drawings. However, the health condition diagnosis unit is a computer that is connected to the brain wave measuring unit in order to receive the brain waves measured in the brain wave measuring unit, and performs a health condition diagnosing method as illustrated in the flowcharts of FIGS. 3 and 4 through an algorithm and a database that are stored in the health condition diagnosis unit.

FIG. 1 is a block diagram illustrating a brain wave measuring unit that measures and processes brain waves that are applied in a health diagnosis apparatus and method using the brain wave pattern analysis.

The brain wave measuring unit of FIG. 1 is disclosed in Korean Patent Registration No. 282733 with the same applicant as that of this application, and includes a brain wave detector 20, a signal processor 22, and a serial port 28, all of which are built in a headband.

The brain wave detector 20 uses a plurality of electrodes and detects brain wave signals of four channels at predetermined locations of the scalp of a human head that is to be diagnosed. The brain wave detector 20 according to an embodiment of the present invention includes a two-channels headband and two-channels cup-shaped electrodes. The two-channels headband simply and conveniently measures brain waves from the frontal lobe of the human body, and the two-channels cup-shaped electrodes selectively measure brain waves from locations other than the frontal lobe of the human body, that is, locations such as the parietal lobe, the temporal lobe, and the occipital lobe of the human body.

The signal processor 22 is connected to the brain wave detector 20 by means of a flexible printed circuit board (PCB) on the headband in order to prevent noise. The signal processor 22 includes an amplifier 23, an analog to digital (A/D) converter 24, an encoder 25 and a computer interface 26. As shown in FIG. 2, the amplifier 23 of the signal processor 22 includes a pre-amplifier 232, a filter (not shown), and a main amplifier 234. The pre-amplifier 232 of the amplifier 23 primarily amplifies the amplitude of the weak brain wave signals that have been sensed by the brain wave detector 20 and filters the brain wave signals to eliminate noise. The main amplifier 234 of the amplifier 23 amplifies the brain wave signals filtered by the pre-amplifier 232 by approximately 50,000 times. The A/D converter 24 of the signal processor 22 samples the amplified brain wave signals at a rate of 1,024 samples per second and converts the sampled brain wave signals into digital values. The encoder 25 of the signal processor 22 encodes an identifier of each of the four channels with a digital value of one byte for each of the four channels in sequence on a real-time basis. The computer interface 26 of the signal processor 22 transmits the encoded result of the encoder 25 to the serial port 28, which can be a universal serial bus (USB) port or a serial port of a computer in a wire or wireless mode.

The serial port 28 is connected to the signal processor 22 by a wire. A 9-pin connector or 25-pin connector of an RS232-C method is used as the serial port 28, so as to be connected with a serial port of a computer. Also, the serial port 28 can be connected to the USB port of a computer.

FIG. 2 is a schematic diagram illustrating an amplifier in a headband adhered to the frontal lobe of a human head for measuring and extracting brain waves, according to an embodiment of the present invention. In the present embodiment, electrodes, which are used in the headband, are gold plated electrodes and can be directly adhered to the forehead without using a paste. A first electrode 10 and a second electrode 12 in the headband are active electrodes measuring brain waves from the frontal lobe of the left and right sides of the brain. A third electrode 14 in the headband measures brain waves from the right-central side of the forehead and is a reference electrode to which the first and second electrodes 10 and 12 refer. A fourth electrode 16, which is worn on the ear of an individual, becomes a base electrode for the brain waves measured on the scalp. The brain wave electrical potentials of the frontal lobe of the left and right sides of the brain are calculated through Equations 4 and 5.

$$VL=(V1-V4)-(V3-V4) \qquad \text{[Equation 4]}$$

$$VR=(V2-V4)-(V3-V4) \qquad \text{[Equation 5]}$$

Here, VL denotes a left-side brain electrical potential, and VR denotes a right-side brain electrical potential. V1 through V4 denote an electrical potential of the respective first through fourth electrodes.

The present invention performs a health diagnosis function using the brain waves measured as described above, which will be shown in FIG. 3.

The health diagnosis apparatus for respective frequencies is shown in FIG. 3 according to an embodiment the present invention and performs a fast-Fourier-transform (FFT) of brain wave data measured in the frontal lobe of the human body that is to be diagnosed, so as to then classify the brain wave data according to respective frequencies of the brain wave data, and accumulates the classified brain wave data for a predetermined time to thus obtain a repeated particular frequency. The health diagnosis apparatus includes a brain wave measuring unit 30 that measures brain waves, an FFT converter 32 that fast-Fourier-transforms the measured brain waves, a brain wave data accumulator 34 that classifies the brain wave data according to respective frequencies of the brain wave data during the opened eyed state and the closed eye state so as to sequentially accumulate the brain wave data, a pattern analyzer 36 that searches for a repeated particular frequency and a pattern thereof from the accumulated brain wave data, a pattern data comparing unit 38 that correspondingly correlates respective portions of the human body with the respective frequencies of the brain wave data based on the frequency pattern, and a health status analyzer 40 determining the health condition of the human body.

FIG. 4 illustrates a flowchart illustrating a health condition diagnosis method that finds an inflection frequency and analyzes the number of inflections and amplitude of brain wave signal, and a full width at half maximum (FWHM) value of the brain wave signal, so as to then compare the analyzed result with that of a frequency-based human body correspondence database.

Referring to FIG. 4, the brain waves that have been measured from a brain wave measuring unit that is adhered to the frontal lobe, which is located at an area of the forehead of the human body, are transmitted to a computer via a serial communication method or an USB communication method so as to then be fast-Fourier-transformed (S300). During the measurement of the brain waves, the human body that is to be diagnosed is made to repeatedly alternate between an eyes-open state and an eyes-closed state, so as to thereby collect the brain wave data through which appearance and disappearance of a basic rhythmic movement and disappearance states of respective bands can be observed, and the measured data is accumulated for a predetermined time (S310). Thus, an inflection point is discovered according to the frequency on an hourly basis and the repetitively occurring inflection frequency is extracted, so as to thereby analyze a frequency pattern (S320).

The health condition of the human body is determined from the extracted inflection frequency according to a database of respective portions of the human body having a one-to-one correspondence relationship with the respective frequencies discovered from clinical test results. Here, the inflection frequency represents a frequency at a vertex at the point where a first differential value according to the frequency is obtained and whose slope sign value changes relative to the first differential value.

The following Table 1 illustrates an example of a frequency-based human body correspondence database.

TABLE 1

| Band | Frequency | Corresponding point of human body |
| --- | --- | --- |
| Delta wave | 0.1-3 Hz | Eye, eyelid, eyeball, eyeball muscle, facial muscle, nose, mouth, nape of the neck, epilepsy, or a brain-damage |
| Theta wave | 4-7 Hz | Shoulder, ear, eye, face, nose, mouth, or ear noise |
| Alpha wave | 8-12 Hz | Stomach, intestines, genital organs, womb, waist, or kidney |
| SMR wave | 12-15 Hz | Neck, bronchus, lung, heart, dermatosis, or atopic disease |
| Low beta wave | 16-20 Hz | Diaphragm, kidney, teeth, jaw, or cervical spine |
| High beta wave | 21-30 Hz | Cervical spine, hand, foot, or leg |

As illustrated in Table 1, the respective brain wave bands have a specific frequency band, respectively. Each specific frequency band can correspond to a human body corresponding portion on a one-to-one basis. The brain wave band of 0.1-3 Hz is a delta wave band, which corresponds to the eye, eyelid, eyeball, eyeball muscle, facial muscle, nose, mouth, nape of the neck, epilepsy, or a brain-damage. The brain wave band of 4-7 Hz is a theta wave band, which corresponds to the shoulder, ear, eye, face, nose, mouth, or ear noise. The brain wave band of 8-12 Hz is an alpha wave band, which corresponds to the stomach, intestines, genital organs, womb, waist, or kidney. The brain wave band of 12-15 Hz is a Sensory Motor Rhythm (SMR) wave band, which corresponds to the neck, bronchus, lung, heart, dermatosis, or an atopic disease. The brain wave band of 16-20 Hz is a low beta wave band, which corresponds to the diaphragm, kidney, teeth, jaw, or cervical spine. The brain wave band of 21-30 Hz is a high beta wave band, which corresponds to the cervical spine, hand, foot, or leg.

The brain or the body is active when a vertex repetitively reoccurs at an identical frequency. The brain wave signal represents the condition of the brain and the muscle signal represents the condition of the body. Each frequency band corresponds to the respective portions of the human body to thereby determine the health condition of the human body. The severity of the health condition of the human body is determined by the number of inflections, the amplitude of the brain wave signal, and the FWHM value of the brain wave signal, in which a vertex occurs. If the vertex continuously occurs at a predetermined frequency in an eyes-opened and eyes-closed state, it can be determined that the symptoms are serious in terms of health condition. The developing stage of a disease is determined by the FWHM value of the brain wave signal. If the FWHM value of the brain wave signal is low, then a disease has locally spread, and if the FWHM value of the inflection frequency is high, then the disease has extensively spread. The health condition can be expressed as $H(n, V, w) = Af(nV/w)$ according to the above-described Equation 3.

Here, n denotes the number of inflections, V denotes an amplitude of the brain wave signal, w denotes an FWHM value of the brain wave signal, A denotes a proportion constant, H denotes a function representing a health condition, and f denotes a function of variables n, V and w. Thus, the severity of a disease at a corresponding portion of the human body corresponding to a predetermined frequency is proportional to the number of reflections, and the amplitude of the brain wave signal, and inversely proportional to the FWHM value of the brain wave signal. And thus, resulting in a linear equation, but also a nonlinear equation.

Accordingly, in operation S330 of the flowchart of FIG. 4, the number of inflections, that is, a frequency in which a vertex occurs is determined. Then, the method proceeds to operation S340 in the case that the frequency is low to thereby obtain the value of the function H. In the case that the value of the function H is high, the human body is determined as experiencing irregular pain or an abnormality (S350). In the case that the value of the function H is low, the condition of the human body is determined as being healthy (S360).

Also, the method proceeds to operation S370 in the case that the frequency is high to thereby obtain a the function H as defined by Equation 3 above. In the case that the value of the function H is low, the human body is determined as experiencing a local abnormality (S380). In the case that the value of the function H is high, the human body is determined as having a local disease (S390).

The invention claimed is:

1. A health diagnosis apparatus for diagnosing health using brain wave pattern analysis from brain wave signals measured in a brain wave measuring unit that measures brain waves via brain wave measuring sensors attached to the frontal lobe of a human body that is to be diagnosed, the health diagnosis apparatus comprising a brain wave analysis computer that receives and fast-Fourier-transforms the measured brain waves, accumulates brain wave data for a predetermined time interval, analyzes a pattern of a signal that occurs at respective frequencies, and sets the analyzed frequency pattern to correspond to the respective portions of the human body, to thereby determine the health condition of the human body, wherein the brain wave analysis computer accumulates the measured brain wave data for the predetermined time to thereby find a point of inflection to discover a curve changing point according to the respective frequencies and to extract the repetitively occurring point-of-inflection frequency, and then determines the health condition of the human body from the extracted inflection frequency using a database storing frequency data of the respective portions of the human body in a one-to-one correspondence relationship with the respective frequencies which are discovered from clinical test results.

2. The apparatus of claim 1, wherein the predetermined time interval for data collection is hourly.

3. A health condition diagnosis method of diagnosing health using brain wave pattern analysis, the health condition diagnosis method comprising:

adhering a two-channels brain wave measuring sensor to the frontal lobe of the human body to thus measure brain waves in which an ear-clip is a base electrode and the forehead center is a reference electrode;

fast-Fourier-transforming the measured brain waves;

accumulating the fast-Fourier-transformed data for a predetermined time;

analyzing a pattern of a signal with respective frequencies; and setting the analyzed frequency pattern to be in a one-to-one correspondence relationship with the respective portions of the human body using a brain wave analysis computer, to thereby determine the health condition of the human body, wherein the pattern analysis operation comprises discovering an inflection point after a predetermined time interval of data collection according to the respective frequencies, and extracting a repetitively occurring inflection frequency.

4. The health condition diagnosis method of claim 3, wherein the health condition determination is performed using a health condition determination equation of human bodies in which a relative severity of a disease at the corresponding portion of the human body corresponding to a certain frequency is proportional to the number of inflections and amplitude of the brain wave signal and is inversely proportional to a full width at half maximum (FWHM) value of the brain wave signal, according to the number of inflections and amplitude of the brain wave signal, and the FWHM value of the brain wave signal.

5. The method of claim 4, in which the brain waves are measured during alternating eye-open and eye-closed states.

6. The method of claim 4, wherein the brain wave measurements are made from the frontal lobes of the left and right side of the brain.

7. The method of claim 4, wherein the predetermined time interval for data collection is hourly.

8. The method of claim 3, in which the brain waves are measured during alternating eye-open and eye-closed states.

9. The method of claim 3, wherein the brain wave measurements are made from the frontal lobes of the left and right side of the brain.

10. The method of claim 3, wherein the predetermined time interval for data collection is hourly.

* * * * *

UNITED STATES PATENT AND TRADEMARK OFFICE
CERTIFICATE OF CORRECTION

| | | |
|---|---|---|
| PATENT NO. | : 7,756,575 B2 | Page 1 of 1 |
| APPLICATION NO. | : 12/066326 | |
| DATED | : July 13, 2010 | |
| INVENTOR(S) | : Pyong-Woon Park | |

It is certified that error appears in the above-identified patent and that said Letters Patent is hereby corrected as shown below:

On the Title page,

Item (73), Assignee information should be:

Assignee:  Braintech Corporation, Daejeon-City (KR)
                    Korea Research Institute of Jungshin Science, Seoul (KR)

Signed and Sealed this

Twenty-first Day of September, 2010

David J. Kappos
*Director of the United States Patent and Trademark Office*